United States Patent [19]

Fischer et al.

[11] 4,275,031
[45] Jun. 23, 1981

[54] AGENT AND PROCESS FOR CARRYING OUT COLORIMETRIC OR PHOTOMETRIC DETERMINATIONS

[75] Inventors: Wolfgang Fischer; Brigitte Wissel, both of Darmstadt, Fed. Rep. of Germany

[73] Assignee: Merck Patent Gesellschaft mit beschränkter Haftung, Darmstadt, Fed. Rep. of Germany

[21] Appl. No.: 36,709

[22] Filed: May 7, 1979

[30] Foreign Application Priority Data

May 5, 1978 [DE] Fed. Rep. of Germany ....... 2819645

[51] Int. Cl.³ .................... G01N 21/03; G01N 31/22
[52] U.S. Cl. .................... 422/57; 23/230 B; 23/230 R; 23/901; 422/58; 422/102; 422/61; 435/291; 435/805; 435/810
[58] Field of Search .................... 422/55–58, 422/61, 102; 435/287, 288, 289, 291 E, 805, 810; 428/520

[56] References Cited

U.S. PATENT DOCUMENTS

| | | | |
|---|---|---|---|
| 3,701,633 | 10/1972 | Davis | 422/58 |
| 3,768,978 | 10/1973 | Grabb et al. | 422/57 |
| 3,937,613 | 2/1976 | Rosicky | 422/57 |
| 3,980,436 | 9/1976 | Greenfield et al. | 422/61 X |

FOREIGN PATENT DOCUMENTS

| | | | |
|---|---|---|---|
| 1037725 | 8/1958 | Fed. Rep. of Germany | 422/57 |
| 2818826 | 11/1978 | Fed. Rep. of Germany | 422/57 |

*Primary Examiner*—Michael S. Marcus
*Attorney, Agent, or Firm*—Millen & White

[57] ABSTRACT

An agent for use in a colorimetric or photometric determination in aqueous solution comrpises:
   a molded substrate made of non-absorbent, water-insoluble material; and
   a coating thereon of a solid or waxy organic polymer which dissolves in water to form an optically clear solution;
   said polymeric coating having a reagent for the determination embedded therein.

2 Claims, 3 Drawing Figures

AGENT AND PROCESS FOR CARRYING OUT COLORIMETRIC OR PHOTOMETRIC DETERMINATIONS

BACKGROUND OF THE INVENTION

The present invention relates to a new agent and to a new process for carrying out colorimetric or photometric determinations.

Colorimetric or photometric determinations are frequently used in analytical chemistry and especially in medical laboratory diagnostic tests. They are particularly adaptable to series investigations, for which practical and rapid handling even by untrained personnel and rapid evaluation are important.

There has been no lack of attempts to simplify such methods which in essence are based on chemical reactions which are complicated in some cases. As a result, one-run tests and, in particular, also disposable measuring cuvettes have been developed. Disposable cuvettes contain all necessary reagents and contain enzymes, for example, in a freeze-dried form. It is necessary only to add the test solution (for example a body fluid such as serum or urine) and carry out the colorimetric or photometric measurement.

However, even the disposable cuvettes still have considerable disadvantages. Thus, for example, it is frequently difficult to produce a tight seal. Especially in the case of sensitive reagents this becomes noticeable in an unpleasant manner. Moreover, the disposable cuvettes are expensive to produce.

SUMMARY OF THE INVENTION

Accordingly it is an object of the present invention to simplify further the way in which colorimetric and photometric methods are carried out in practice and to avoid the disadvantages of previously known embodiments, especially the mentioned disadvantages of disposable cuvettes.

Upon further study of the specification and appended claims, further objects and advantages of this invention will become apparent to those skilled in the art.

These objects have been achieved by providing the new agent and methods of this invention.

It has been found that reagents for colorimetric or photometric determinations can advantageously be applied to molded supports which consist of nonabsorbent, water-insoluble material. The reagents are embedded on the support in solid or waxy organic polymers, which form an optically clear solution with water. Due to this embedding, the reagents are protected against atmospheric influences such as humidity and have a better shelf life than in the freeze-dried form.

The process of this invention is carried out by immersing the coated molding into the aqueous solution to be tested, whereupon the polymers are dissolved and the reagents are liberated and made to react. The manner of bringing all reactants together is not critical. The solution to be tested can be located in a special reaction vessel in which the reaction with the reagent takes place; an aliquot portion of the mixture can then be transferred from the reaction vessel to the measurement vessel (for example a cuvette) which is used for the actual measurement. However, it is also possible to introduce the test solution initially into the measurement vessel; then the coated molding is immersed and, after the reaction has ended, the measurement is carried out in the same vessel.

If undissolved materials are to be tested (for example in histology), the mixture formed by dissolving the reagents is dripped onto the material, or a reagent film is applied (after moistening the section to be examined). The solvent then dissolves the reagents and feeds them to the substances to be detected. After waiting until the reaction time has elapsed, these substances are clearly discernible by the appearance of a color. The intensity of the color is dependent on the amount and the activity of the substances. In this case the evaluation is generally made under a microscope.

Thus, the present invention relates to an agent for carrying out colorimetric or photometric determinations in aqueous solution, comprising moldings made of nonabsorbent, water-insoluble material coated with reagents, wherein the reagents are embedded, on the molding, in solid or waxy water soluble organic polymers which form an optically clear solution with water.

The invention also relates to a process for carrying out colorimetric or photometric determinations in aqueous solution using moldings made of non-absorbent, water-insoluble material coated with reagents, wherein the reagents are embedded on the molding in solid or waxy organic polymers which form an optically clear solution with water and are liberated, prior to the actual determination, by dissolving the polymer.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCUSSION

Figure 1:
FIG. 1 shows a film-shaped agent of this invention having a single reagent-containing coating and adapted as a cuvette.

Herein, the expression "soluble in water to give an optically clear solution" means that the solutions of the embedment polymers must have no adverse influence on the optical characteristics of the solution to be measured (for example no characteristic absorption) in the measurement range.

The moldings can be of any type, shape and size. Preferably, films or rods are used; in principle, any desired moldings can be employed if they are suitable for the process of this invention. Thus, for example, small tubes, sheets, spheres, tubing and the cuvettes themselves can be used as moldings. As rods, those having a circular, square or rectangular cross-section are preferred since these are the most simple to coat, pack and use.

The size of the moldings is not critical and is appropriately suited to the particular intended use, for example, to the shape and size of the cuvettes used for the optical determination. When films are used, the thickness is not critical; for practical reasons it is generally between about 0.1 and about 1 mm.

For example, when cuvettes 10×10×50 mm in size are used, pieces of film or rods 9×80×0.2 mm in size are appropriately employed. On the other hand, for example, round rods about 75 mm in length and 3 mm in diameter are also suitable for the same purpose. If the cuvettes or reaction vessels are larger, the dimensions of the moldings are correspondingly larger, and if they are smaller the dimensions of the moldings are correspondingly smaller. With these dimensions, after the reagent coating has dissolved, the films or rods can also be used for mixing the reaction solution, for example, by stirring or moving up and down.

The material from which the moldings are made must be of such a nature that no reagents are absorbed therein or held fast thereto. Thus, non-absorbent refers inter alia to non-absorption of the embedded reagents. Therefore, for example, absorbent supports, such as are customarily used for reagent papers or reagent strips, cannot be used. Furthermore, the material should be insoluble in water, so that it can be removed cleanly from the solution. In other respects, however, the choice of the material for the moldings is not critical. For example, suitble such substrates include water-insoluble plastics, for example polymers and polycondensation products, such as polyvinyl chloride (PVC), polyesters (for example polyethylene terephthalate), polyamides, polycarbonates, polystyrene, polyurethanes and polyalkylenes, such as polyethylene or polypropylene; other high molecular weight organic materials such as cellulose acetate; and also metals, such as steel, nickel or aluminum; glass; porcelain or other ceramic materials; and the like.

These moldings can be coated, for example, by spreading, immersing, spraying or printing, and subsequently drying the coating. The organic polymer coating thickness is not critical and generally is 0.01—1 mm.

Suitable organic polymers for use as the embedment coating, which polymers form an optically clear solution with water, include preferably solid or waxy polyvinylpyrrolidones (PVP), polyvinyl alcohols, polyethylene glycols and/or polyethyleneimines, and also copolymers which dissolve in water to given an optically clear solution, for example vinylpyrrolidone/vinyl acetate copolymers. These polymers preferably have molecular weights of between about 1,000 and about 1,000,000. A preferred polymer is, for example, PVP with molecular weights between about 10,000 and about 1,000,000 and K values (determined in 1% aqueous solution with an Ubbelohde viscometer) between about 20 and 100. Further polymers which are suitable for use according to the invention are, for example, polyvinyl alcohols with molecular weights of between about 10,000 and about 200,000 and viscosities between 3 and about 50 cP (in 4% aqueous solution at 20° C.). Among the polyethylene glycols, those with molecular weights between about 1,000 and about 1,000,000 are very suitable; thus, for example, commercially available polyethylene glycol with an average molecular weight of 3,800–4,800 (solidification point 53°–58° C.; $n_D^{25}$ 1.455; viscosity at 25° of 90–120) can be used. A preferred commercially available polyethyleneimine has, for example, a density $d_{20}$ of about 1.07, a viscosity of about 10,000–20,000 cP (according to Brookfield; at 20° C. at 20 rpm) and a pH value of about 12. Among the vinylpyrrolidone/vinyl acetate copolymers, suitable polymers are, for example, those in which the proportion of vinylpyrrolidone is 20–99 mole percent and the proportion of vinyl acetate is accordingly 80–1 mole percent; these polymers have, for example, K values between 15 and 40 and especially between 19 and 34.

The agents of this invention can be employed in many fields, for example, in the analysis of metals and ores (compare, for example, O. G. Koch and G. A. Koch-Dedic, Handbuch der Spurenanalyse (Handbook of Trace Analysis), Springer-Verlag, Heidelberg, 1974)); in the testing of drinking water, water for industrial use and effluents (compare, for example, GdCh (Society of German Chemists), Deutsche Einheitsverfahren zur Wasser-, Abwasser- und Schlamm-Untersuchung (German Standard Methods for the Testing of Water, Effluents and Sludge), Verlag Chemie, Weinheim, 1975); in the analysis of foodstuffs and in hygiene monitoring (compare, for example, J. Schormüller, Handbuch der Lebensmittelchemie (Handbook of Foodstuffs Chemistry), Springer-Verlag, Heidelberg); in chemical analysis in other fields; in medical diagnosis (compare, for example, H. H. Bergmeyer, Methoden der enzymatischen Analyse (Methods of Enzymatic Analysis), Verlag Chemie, Weinheim, 1974); and in histochemistry (compare, for example, Chayen, Bitensky and Butcher, Histochemie (Histochemistry), Verlag Chemie, Weinheim, 1975).

More specifically, examples of substances which can be determined according to this invention include: inorganic substances; cations and anions, such as aluminum (with alizarinsulphonic acid, aurin tricarboxylic acid, Chromazurol S, Eriochrome cyanin or 8-hydroxyquinoline), antimony [with Rhodamine B or silver diethyldithiocarbamate (silver DDC)], arsenic (with silver DDC), beryllium (with aurin tricarboxylic acid, Chromazurol S or Eriochrome cyanine), lead (with dithizone or sodium DDC), boron (with 1,1'-dianthrimide), cadmium (with dithizone), calcium (with murexide), cerium (with 8-hydroxyquinoline), chlorine (with N,N-diethyl-p-phenylenediammonium sulphate), chromium (with diphenylcarbazide), iron (with bathophenanthroline, bathophenanthrolinedisulphonic acid, dimethylglyoxime, 2,2'-bipyridine, Nitroso R salt, 1,10-phenantrolinium chloride, sulphosalicylic acid or thioglycollic acid), gold (with pyoctanine, rhodamine B or o-tolidine), indium (with dithizone), iodine (with o-tolidine), cobalt (with 1-nitroso-2-naphthol, 2-nitroso-1-naphthol, Nitroso R salt or rubeanic acid), copper (with 2,2'-biquinoline, neocuproin, bathocuproine, lead DDC, diethylammonium DDC, sodium DDC, oxalyl dihydrazide, oxalic acid bis(cyclohexylidene hydrazide) or rubeanic acid), magnesium (with eriochrome black T), manganese (with formaldoxime or sodium DDC), molybdenum (with phenylfluorone or toluene-3,4-dithiol), nickel (with dimethylglyoxime or rubeanic acid), niobium [with 4-(2-pyridyl-azo)-resorcinol], nitrate [with N-(1-naphthyl)-ethylenediammonium dichloride], nitrite (with sulphanilic acid and 1-naphthylamine or with other azo dye components), osmium (with diphenylcarbazide), palladium (with Bismuthiol I, Nitroso R salt or 2-nitroso-1-naphthol), platinum (with dithizone), mercury (with dithizone), rhodium [with 1-(2-pyridyl-azo)-2-naphthol], scandium (with alizarinsulphonic acid), selenium (with 3,3'-diaminobenzidinium tetrachloride), sulphate (with N,N-dimethyl-p-phenylenediammonium dichloride), sulphide (with N,N-dimethyl-p-phenylenediammonium dichloride), thallium (with brilliant green, crystal violet or Rhodamine B), titanium (with pyrocatechol-3,5-disulphonic acid or chromotropic acid), uranium [with glyoxal bis (2-hydroxy-anil) or 1-(2-pyridylazo)-2-naphthol], vanadium (with Variamine blue, sodium DDC or N-benzoyl-N-phenylhydroxylamine), bismuth (with Bismuthiol I, xylenol orange or dithizone), zinc [with dithizone, 1-(2-pyridylazo)-2-naphthol or Zincon], tin (with phenylfluorone) and zirconium (with phenylfluorone or xylenol orange).

Furthermore, important diagnostic and biochemical determinations can also be carried out according to this invention. Examples include determinations of: alkaline phosphatase (with p-nitrophenyl phosphate), α-amylase (with amylose/iodine), inorganic phosphate (with molybdate/reducing agent), ascorbic acid (with 2,6-dichlorophenolindophenol), bilirubin (with diazotized sulphanilic acid), blood sugar (with glucoseoxidase/peroxidase/4-aminoantipyrine, cholesterol (with cholesterol-oxidase/iodide), cholinesterase (with 5-butyl-thiocholine iodide/5,5′-dithio-bis-2-nitrobenzoic acid), creatine kinase (CK; with creatine phosphate/ADP/glucose/hexokinase/NADP/glucose-6-phosphate dehydrogenase), creatine-kinase-isoenzyme MB (CK-MB: as creatine-kinase, but with the addition of inhibiting antibodies), creatinine (with picric acid), iron binding capacity (EBC: determination of non-bonded iron with sulphonated bathophenanthroline), total protein (with copper sulphate), glutamate dehydrogenase (GLDH; with 2-ketoglutarate/NADH/ADP), glutamate-oxaloacetatetransaminase (GOT; with 2-ketoglutarate/aspartate/NADH/LDH/MCH), glutamate-pyruvate-transaminase (GPT; with 2-ketoglutarate/L-alanine/lactate dehydrogenase/NADH), γ-glutamyl-transferase (γ-GT; with L-γ-glutamyl-3-carboxy-4-nitroanilide/glycylglycine), hemoglobin (with $KCN/K_3[Fe(CN)_6]$), uric acid (with uricase/catalase/copper sulphate/bathocupreindisulphonic acid), urea (with urease/phenol/NaOCl or with diacetylmonoxime/thiosemicarbazide), 2-hydroxybutyrate dehydrogenase (HBDH; with 2-oxobutyrate/NADH), lactate dehydrogenase (LDH: with pyruvate/NADH), leucine-aryl-amidase (with L-leucine-4-nitroanilide), magnesium (with xylidyl blue), acid phosphatase (with p-nitrophenyl phosphate) and triglycerides (with lipase-/esterase/glycerokinase/pyruvate kinase/LDH-/NADH/phosphoenol pyruvate/ATP).

Furthermore, in histochemistry or cytochemistry, detection of the following substances, for example, can be carried out according to this invention: nucleic acids (Feulgen reaction), polysaccharides (PAS method), cytochromeoxidase (Nadi reaction), peroxidase (benzidine/$H_2O_2$), phosphatase (naphthyl phosphate/diazonium salt), esterase (indoxyl acetate method or naphthyl acetate/diazonium salt), succinate-dehydrogenase (succinate/tetrazolium salt), glutamate-dehydrogenase (glutamate/tetrazolium salt) and lactate-dehydrogenase (lactate/tetrazolium salt).

The reagents suitable for use in this invention, of course, must not react either with the film material or with the organic polymer in which they are embedded but, otherwise, are subject to no restrictions. The reagents which can be used are as a rule substances which have characteristic absorption maxima in the visible or the ultraviolet range, or precursors for forming such substances. Other substances which can be used as reagents are very diverse auxiliaries, for example, enzymes, oxidizing agents or reducing agents, acids, bases or salts, which, for example, can be employed as buffers.

The reagents can be embedded in the polymer coating by coating the molded substrate via a solution of the polymer and the reagent(s) in a suitable solvent. Suitable solvents for use when embedding substances on the support (for example on the film) include, for example, water and organic solvents, which, however, must not dissolve the material of the molding, for example alcohols, such as methanol, ethanol or isopropanol; ketones, such as acetone; amides, such as dimethylformamide; sulphoxides, such as dimethylsulphoxide; or other aprotic solvents. The last-mentioned solvents are generally not completely removed upon drying but are at least partially retained in the embedded substance. Thus, they can act as solubilizing agents when the embedded substance is subsequently dissolved.

The quantity (weight) ratio of reagent to polymer can vary within wide limits and is not critical. In general it is between 10:1 and 0.1:1.

Reagents which are not compatible with one another can be added successively on separate films but can also be applied alongside one another (spatially separated) on one film.

The cuvettes can be designed as "disposable articles." Thus, for example, there can be one cuvette and one film (or one rod) for each test, the shape and size of the film (or of the rod) being matched to the cuvette. After carrying out the test, the kit can be thrown away.

The agents of this invention, (especially films), can also be employed in automatic analyzers. Additionally, it is often appropriate to incorporate identifying coding (for example, the type of measurement, the measurement wavelength, the reaction temperature and reaction time, etc.) in the upper section of the film or other molding.

A particular embodiment of this invention (compare FIG. 1) comprises applying the reagent/polymer solution in the form of a streak to the film 1 and then sealing (sticking or welding) a second film 2 over the reagent zone 3 in such a way that a hollow space 4 which is of defined thickness and open on two sides remains between the two films above the reagent zone 3. On immersion in the solution to be tested, the solution fills the hollow space and dissolves the reagents out. The color reaction which then takes place can be evaluated colorimetrically or photometrically. Thus, the "cuvette" to be used for the measurement is formed on the film itself and is thus a constituent of the film ("cuvette film"). The "reagent film" and the "cuvette" thus form a single unit. The hollow space is preferably of rectangular cross-section and in this space the distance between the two films is about 0.1 to 10, and preferably 1–3 mm.

Figure 2:
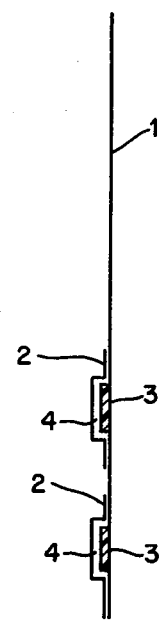
FIG. 2 shows such a cuvette having two reagent-containing coatings.

Several reagent zones 3 with welded-on films 2 can be arranged above one another on the "base film" 1, forming a reagent film for multiple analyses (simultaneous determination of different constituents) (compare FIG. 2).

Figure 3:
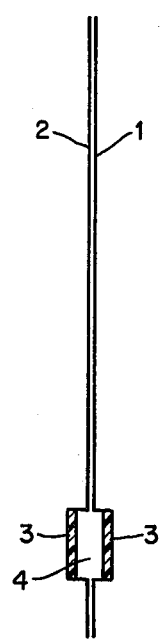
FIG. 3 shows a cuvette formed by sealing two preformed film type agents of the invention.

To obtain a uniform distribution of the reagents, it can sometimes be advantageous (compare FIG. 3) to form the hollow space 4 by sealing two shaped films 1 and 2, after, in each case, prior drying of the reagent solution or solutions in the depressions of the two films.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

The PVP used in the following examples is a commercial preparation (Luviskol® K 90) with a molecular weight of about 700,000 and a K value of 92±4.

EXAMPLE 1

Reagent film for the determination of glucose

A solution which is composed of the following four individual solutions is prepared:
(1) 100 g of polyethyleneimine (Polymin® P) are dissolved in 240 ml of water. The pH value of the solution is adjusted to 5.3 by adding 32% hydrochloric acid (consumption: about 65 ml).
(2) 14.4 g of glucoseoxidase (12 U/mg) and 0.4 g of peroxidase (60 U/mg) are dissolved in 400 ml of water.
(3) 4.8 g. of tetramethylbenzidine and 34 g of PVP are dissolved in 400 ml of ethanol.
(4) 0.2 g of ascorbic acid is dissolved in 100 ml of water.

With the aid of a sponge, this solution is spread uniformly on a 7 cm high and 0.2 mm thick transparent PVC film so that a 10 mm high zone forms at the lower end of the film. After drying at 60°-80° C. (10 minutes), the film is cut into strips 9 mm wide.

For analysis, a strip of this type, which can be held by its upper end, is placed with the reagent zone in the cuvette, which is filled up to a mark with the liquid to be tested. In order to accelerate the dissolving process, the film is moved backward and forward several times. After a waiting time of 10 minutes, the colorimetric determination is carried out in the customary manner at 640 nm.

EXAMPLE 2

Reagent film for the determination of hydrogen peroxide.

A transparent PVC film (7 cm high and 0.2 mm thick) is coated with a mixture of the following four individual solutions:
(1) 30 g of polyethyleneimine (Polymin® P) are dissolved in 56 ml of water. The pH value of the solution is adjusted to 5.5 by adding 32% hydrochloric acid (consumption: about 19 ml).
(2) 1.2 g of tetramethylbenzidine and 12 g of PVP are dissolved in 120 ml of ethanol.
(3) 3.5 mg of peroxidase (100 U/mg) are dissolved in 35 ml of water.
(4) 10 mg of ascorbic acid are dissolved in 10 ml of water.

In other respects the procedure is analogous to Example 1 (measurement at 640 nm).

EXAMPLE 3

Reagent film for the determination of ascorbic acid.

The following two reagent solutions are prepared and sprayed above one another (spatially separated) on a film (transparent PVC, height: 7 cm; thickness: 0.2 mm), each over a 15 mm broad strip with a 5 mm interspace.
(1) 10 g of malonic acid and 5 g of a vinylpyrrolidine/vinyl acetate copolymer (Luviskol®-VA 73 E; vinylpyrrolidone:vinyl acetate ratio 70:30; K value 34±4) are dissolved in 100 ml of ethanol.
(2) 1.5 g of 2,6-dichlorophenol-indophenol (sodium salt) and 3 g of vinylpyrrolidone/vinyl acetate copolymer are dissolved in 100 ml of ethanol.

In other respects the procedure is analogous to Example 1 (measurement at 520 nm).

EXAMPLE 4

Reagent film for the determination of nitrite 30 g of 2-amino-4-(2-hydroxyethylsulphonyl)-benzoic acid, 5.5 g of N-naphth-1-yl-ethylenediammonium oxalate, 77 g of tartaric acid and 50 g of polyethylene glycol ("PEG 4000" according to DAB 7) are dissolved successively in a mixture of 200 ml of water and 500 ml of methanol. Using this solution, a PVC film is coated as in Example 1. In other respects the procedure is analogous to Example 1 (measurement at 525 nm).

EXAMPLE 5

Reagent film for the determination of divalent iron 10 g of 1,10-phenanthrolinium chloride, 10 g of triethanolamine and 5 g of PVP are dissolved successively in a mixture of 20 ml of water and 80 ml of ethanol. Pieces of polyester film (polyethylene terephthalate; size 9×0.2×80 mm) are immersed 30 mm deep into this solution and are then dried at 70° (for 10 minutes).

For the actual determination, 3 ml of the solution to be tested are filled into cuvettes (10×10×50 mm), a peice of film is immersed and PVP and reagent are dissolved by moving the film up and down several times. A red to brown colored solution is obtained, depending on the amount of $Fe^{++}$ ions present, and the extinction of this solution is measured at 510 nm after 5 minutes.

EXAMPLE 6

Reagent film for the determination of chlorine

Two coating solutions are prepared:
(1) A solution of 10 g of sodium acetate in 80 ml of methanol is mixed with a solution of 3 g of polyvinyl alcohol (Mowiol® N 50-88) in 20 ml of water.
(2) A solution of 3 g of N,N-diethyl-p-phenylenediammonium sulphate in 10 ml of dimethylsulphoxide and 50 ml of ethanol is mixed with a solution of 5 g of polyvinyl alcohol in 40 ml of water.

One of these coating solutions is applied to the front and the other to the back of a 90 mm broad and 1,000 mm long film band (PVC, thickness 0.2 mm) with the aid of a roller, each solution being applied as a 20 mm broad coating. After drying (10 minutes at 60°-80° C.), the film band is cut into 10 mm broad strips and in other respects the procedure followed is analogous to Example 1 (measurement at 680 nm).

EXAMPLE 7

Reagent film for the determination of 2-hydroxybutyrate dehydrogenase

Two coating solutions are prepared:
1. A solution of 5 g of PVP in 40 ml of water, 50 ml of a 10% phosphate buffer solution (pH 7.5) and a solution of 3 g of ethoxylated nonylphenol (Marlophen® 812) in 10 ml of ethanol are mixed.
2. A solution of 5 g of NADH and 2.5 g of sodium 2-oxobutyrate in 30 ml of 0.2% $NaHCO_3$ solution is mixed with a solution of 5 g of PVP in 70 ml of ethanol.

The two solutions are applied as two coatings, each 15 mm broad, (at a distance of 5 mm) by screen printing to an 80 mm broad and 500 mm long film strip (of cellulose acetate, thickness 0.3 mm). In other respects the procedure is analogous to Example 1 (measurement of the differences in extinction per minute at 365 nm).

EXAMPLE 8

Reagent film for the determination of nitrite

The lower end of a polyester film (200×1,000 mm) is uniformly coated along a 30 mm broad strip by means of a roller with the reagent solution according to Example 4. After drying, the film is cut into 12 mm broad strips. A color comparison scale is prepared by filling test tubes (size 15×⅜mm) each with 10 ml of an aqueous sodium nitrite solution, the solutions having the following concentrations: 0.01; 0.05; 0.1; 0.3; 0.5; 0.7; 1.0; 3.0; 5.0 and 10.0 mg/l. A reagent film is added to each tube and the mixtures are stirred well. After 3 minutes stable reaction colors have developed, so that the color scale for comparison is ready. 10 ml of the solution to be tested are filled into a test tube (size 15×160 mm). A reagent film is immersed and the mixture is stirred well and the nitrite concentration is determined after 3 minutes, by color comparison.

EXAMPLE 9

Reagent rods for the determination of ascorbic acid (a) Preparation of the rods

Glass rods (size 3×75 mm) are dipped 32 mm deep into reagent solution (2) according to Example 3 for 3 seconds and dried in a stream of air. The reagent is dissolved from the lower end again by then dipping the rods 17 mm deep into warm water at 25° for 5 minutes. Finally, after drying again, the rods are dipped 15 mm deep into reagent solution (1) according to Example 3 and are again dried in a stream of air.

(b) Method for carrying out the determination 3.0 ml of the solution to be tested are filled into a cuvette (10×10×50 mm). One of the rods prepared according to (a) is added to this solution. By stirring (for one minute), the substances applied are dissolved down and can now react with the ascorbic acid. The residual color is measured at 520 nm. If the amount of 2,6-dichlorophenol-indophenol present on the rod is not sufficient and the solution consequently remains completely colorless, further reagent is dissolved from a second or third rod until there is a permanent measurable coloration.

EXAMPLE 10

Reagent film for the determination of peroxidase in leucocytes

Pieces of PVC film with dimensions of 24×55 mm (thickness 0.2 mm) are coated uniformly with the following solution: 3.84 g of 4-chloro-1-naphthol and 1 g of PVP in 130 ml of ethanol are mixed with 20.5 ml of a 0.5% solution of sodium perborate in water. After coating, the films are dried.

Use:

An air-dried blood smear is fixed by placing it (for 30 seconds) in a solution of formaldehyde/ethanol (10 ml of 30% aqueous formaldehyde solution +90 ml of 95% ethanol) and rinsed with water. One drop of ethanol is dripped onto the smear while this is still moist and the film is placed on top. After a reaction time of 5 minutes, the film is removed and the smear is rinsed with water and stained for 10 seconds with concentrated Giemsa solution. It is again rinsed with water and dried and finally is evaluated under a microscope: peroxidase-positive leucocytes show dark violet colored granula in plasma.

EXAMPLE 11

"Cuvette film" for the determination of glucose

A transparent and colorless PVC film [size 75×100 mm; (compare 1 of FIG. 1)] is coated analogously to Example 1 in the longitudinal direction along a 10 mm broad zone 5 mm away from the lower edge and dried. A previously shaped second film 2 with dimensions of 20×100 mm is sealed (stuck or welded) onto this film. As a result of the shaping, a hollow space 4 is formed above the reagent zone 3 and this space subsequently takes up the solution to be tested and serves at the same time as a reaction vessel and a cuvette. In the hollow space the distance between the two films is 2 mm. The film is then cut into 10 mm broad strips.

For the actual determination, a strip is held by its upper end and dipped into the solution to be tested so that the solution fills the hollow space. The reagents dissolve and in the presence of glucose form a blue solution. After 10 minutes, the color is evaluated visually by comparison with a color scale or photometrically by measuring the extinction at 640 nm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cuvette for carrying out a colorimetric or photometric determination in aqueous solution consisting essentially of:
    a first film-shaped substrate made of non-absorbent, water-insoluble, optically clear material; and
    a coating thereon of a solid or waxy organic polymer which dissolves in water to form an optically clear solution, said polymeric coating having a reagent for the determination embedded therein;
    wherein the coating on the first substrate is covered by a second film-shaped substrate sealed to the first substrate, said second substrate having a stepped, rectangular cross section thereby forming a hollow space of a thickness of 1–3 mm above said coating, said second substrate being made of non-absorbent, water-insoluble, optically clear material; and said hollow space being open on two sides such that a test solution will flow therethrough and fill the hollow space upon submersion of the cuvette in the solution.

2. A cuvette of claim 1 coated in two locations with a reagent-containing polymeric coating, each location being covered by one of said second film-shaped substrates.

* * * * *